United States Patent [19]

Poindexter

[11] Patent Number: 5,045,156
[45] Date of Patent: Sep. 3, 1991

[54] DISTILLATION OF ISOPHTHALONITRILE WITH A HYDROCARBON LIQUID

[75] Inventor: Michael K. Poindexter, Sugarland, Tex.

[73] Assignee: Nalco Chemical Company, Naperville, Ill.

[21] Appl. No.: 638,932

[22] Filed: Jan. 9, 1991

[51] Int. Cl.$^5$ ............... B01D 3/34; C07C 253/34
[52] U.S. Cl. ............... 203/68; 203/6; 203/52; 203/DIG. 25; 558/327; 558/421
[58] Field of Search ............... 203/6, 7, 8, 9, 68, 203/70, 69, 52, DIG. 25; 558/327, 421

[56] References Cited

U.S. PATENT DOCUMENTS

| | | | |
|---|---|---|---|
| 3,324,011 | 6/1967 | Baum | 203/6 |
| 3,393,220 | 7/1968 | Winnick et al. | 558/327 |
| 3,436,318 | 4/1969 | Glass | 203/68 |
| 3,462,476 | 8/1969 | O'Donnell et al. | 558/327 |
| 4,116,999 | 9/1978 | Barchas | 558/421 |
| 4,134,910 | 1/1979 | Barchas et al. | 558/421 |

FOREIGN PATENT DOCUMENTS 665635  6/1963  Canada ............... 203/7

*Primary Examiner*—Wilbur Bascomb, Jr.
*Attorney, Agent, or Firm*—Robert A. Miller; John G. Premo

[57] ABSTRACT

High boiling point aromatic free hydrocarbon liquids partially substituted for isophthalonitrile during its distillation fluidize the bottoms and increase isophthalonitrile yield.

3 Claims, No Drawings

DISTILLATION OF ISOPHTHALONITRILE WITH A HYDROCARBON LIQUID

INTRODUCTION 1,3-Dicyanobenzene, also known as isophthalonitrile (IPN), is often produced via an ammoxidation involving meta-xylene, oxygen and ammonia over a catalyst. Very high-purity IPN (>99.05%) is required for subsequent processing for certain applications.

Impurities which arise from ammoxidation by-products and supposed dimerization and trimerization of IPN must be removed before further processing is permitted. The dimers and trimers are extremely insolube and if allowed to precipitate will foul the fractional column and reboiler. Leaving a significant portion of IPN in the tower bottoms helps to solubilize and wash away these side-products; this in effect reduces column fouling. There is a serious economic drawback with this mode of operation since IPN is a very profitable compound and using it as a foulant "wash" results in lost profits.

Not only is IPN being lost, but the entire bottoms stream solidifies well above ambient temperature (m.p. of IPN is 324° F.) as it leaves the tower. This makes the stream difficult to handle since upon cooling it becomes brick-like. Currently the bottoms are being landfilled by some producers— a costly solution.

IPN producers would like to increase their production of IPN and find an alternative means for bottoms disposal. Whatever chemical is added to help improve the process, it cannot go overhead. The additive should also be inert towards IPN (e.g., have no nucleophilic moieties).

If it were possible to develop a product which substituted in whole or in part for IPN during the distillation which would increase the recovery of IPN from the bottoms and keep the bottoms fluid and pumpable for disposal by incineration, a valuable contribution to the art would be afforded. Furthermore, the product would reduce maintenance costs by eliminating shutdowns due to foulant accumulation and increase production by increasing operating utility.

THE INVENTION

This invention relates to an improved process of the type wherein a crude IPN is fed to a distillation column and a portion of the IPN being distilled is used to solubilize solid impurities formed during the distillation process and which impurities are removed from the distillation column for disposal. The improvement of this invention comprises substituting from 1 to 50% by weight of the crude IPN feed to the column, a substantially aromatic free hydrocarbon liquid having an initial boiling point between 570° to 750° F. and continuing the distillation whereby the hydrocarbon liquid replaces the IPN used to solubilize the impurities thereby increasing the yield of distilled IPN recovered from the column.

A high boiling, non-aromatic solvent found to be unreactive towards IPN in laboratory testing is described in Table 1. During a field trial, the additive kept the bottoms stream fluid demonstrating that the residue could be easily pumped to an incinerator for disposal. In fact, a bottoms sample obtained during the trial has remained fluid for over six (6) months. It was also found that the IPN yield was increased with no loss in purity.

It is obvious that the improved method described above can be applied to the distillation of liquids other than IPN. It is important, however, that the additive remain inert or non-reactive toward the principal liquid being distilled.

FEED OF THE AROMATIC FREE HYDROCARBON LIQUID AND DOSAGE

As indicated, the hydrocarbon liquid is blended with the crude IPN feed so that from 1 to 50% by weight of the crude IPN is replaced by the hydrocarbon liquid. In most cases the amount of hydrocarbon liquid will replace between 5 to 40% by weight, of the crude IPN fed to the column. The hydrocarbon liquid, while composed primarily of higher mixed aliphatic hydrocarbons, may also contain blends of cycloaliphatic hydrocarbon liquids.

The initial boiling point of the aromatic free hydrocarbon liquids may range from 570° to 750° F. Most of the preferred hydrocarbon liquid will have initial boiling points which range between 580° to 700° F.

EVALUATION OF THE INVENTION

It was found in an extended plant trial that the yield of IPN increased 4.1% for a Table 1 product rate of 4.6 gallons/hour.

TABLE 1

| BOILING RANGE OF PRODUCT* | | |
|---|---|---|
| OBSERVATION | @ 5 MM HG | CORRECTED TO 760 MM HG |
| Initial Boiling Point | 340 | 632 |
| 5% Recovered | 434 | 745 |
| 10% Recovered | 481 | 800 |
| 20% Recovered | 518 | 843 |
| 30% Recovered | 540 | 868 |
| 40% Recovered | 551 | 880 |
| 50% Recovered | 568 | 901 |
| 60% Recovered | 582 | 917 |
| 70% Recovered | 593 | 929 |
| 80% Recovered | 610 | 948 |
| 90% Recovered | 638 | 980 |
| 95% Recovered | 662 | 1007 |
| END POINT | 691 | 1038 |
| RECOVERED | | 98.0% |
| RESIDUE | | 2.0% |

*All temperatures are in degrees Fahrenheit, distillation was run at 5 mm Hg.

I claim:

1. In a process wherein a crude isophthalonitrile (IPN) is fed to a distillation column and a portion of the IPN being distilled is used to solubilize solid impurities formed during the distillation process and which impurities are removed from the distillation column for disposal, the improvement which comprises increasing the yield of IPN by replacing from 1 to 50% by weight of the crude INP feed to the column, with a substantially aromatic free hydrocarbon liquid having an initial boiling point between 570° to 750° F. and continuing the distillation whereby the hydrocarbon liquid replaces the INP used to solubilize the impurities thereby increasing the yield of distilled IPN recovered from the column, and then removing distilled IPN from the column.

2. The process of claim 1 wherein between 5 to 40% by weight of the crude IPN feed to the column is replaced by the substantially aromatic free hydrocarbon liquid.

3. The process of claim 2 where the aromatic free hydrocarbon liquid has an initial boiling point of about 580° F.

* * * * *